(12) United States Patent
Putha et al.

(10) Patent No.: US 11,308,612 B2
(45) Date of Patent: Apr. 19, 2022

(54) SYSTEMS AND METHODS FOR DETECTION OF INFECTIOUS RESPIRATORY DISEASES

(71) Applicant: Qure.ai Technologies Private Limited, Mumbai (IN)

(72) Inventors: Preetham Putha, Guntur (IN); Manoj Tadepalli, Krishna Gudivada (IN); Bhargava Reddy, Hyderabad (IN); Tarun Raj, Vishakapatnam (IN); Ammar Jagirdar, Mumbai (IN); Pooja Rao, Pune (IN); Prashant Warier, Mumbai (IN)

(73) Assignee: Qure.ai Technologies Private Limited, Mumbai (IN)

( * ) Notice: Subject to any disclaimer, the term of this patent is extended or adjusted under 35 U.S.C. 154(b) by 159 days.

(21) Appl. No.: 16/889,412

(22) Filed: Jun. 1, 2020

(65) Prior Publication Data

US 2021/0327055 A1    Oct. 21, 2021

(51) Int. Cl.
*G06T 7/00* (2017.01)
*G06K 9/62* (2006.01)
(Continued)

(52) U.S. Cl.
CPC ............ *G06T 7/0012* (2013.01); *A61B 6/503* (2013.01); *A61B 6/505* (2013.01); *A61B 6/5217* (2013.01);
(Continued)

(58) Field of Classification Search
CPC . G06T 7/0012; G06T 7/11; G06T 7/70; A61B 6/503; A61B 6/505; A61B 6/5217; C12Q 1/689; C12Q 1/701; G06F 40/20; G06F 40/216; G06F 40/247; G06F 40/284; G06F 40/295; G06F 40/30; G06K 9/3241; G06K 9/6256; G06K 9/628; G06K 2207/20076; G06K 2207/20081; G06K 2207/20084; G06K 2207/30061; G16H 10/40; G16H 30/40; G16H 50/20;
(Continued)

(56) References Cited

U.S. PATENT DOCUMENTS

2020/0093455 A1*  3/2020  Wang ..................... G16H 50/70
2020/0294654 A1*  9/2020  Harzig ................. G06F 40/279

OTHER PUBLICATIONS

Fang et al., "Sensitivity of Chest CT for COVID-19: Comparison to RT-PCR", Radiology. Aug. 2020;296(2):E115-E117. doi: 10.1148/radiol.2020200432. Epub Feb. 19, 2020. PMID: 32073353; PMCID: PMC7233365, pp. E115-E117 (Year: 2020).*

(Continued)

*Primary Examiner* — Nay A Maung
*Assistant Examiner* — Jose M Torres
(74) *Attorney, Agent, or Firm* — Wiley Rein LLP

(57) ABSTRACT

This disclosure generally pertains to systems and methods for detection of infectious respiratory diseases by implementation of an automated X-rays-based triage approach alongside algorithmic clinical sample pooling for molecular diagnosis. Certain embodiments relate to methods for the development of deep learning algorithms that perform machine recognition of specific features and conditions in chest X-ray imaging data. The chest X-ray imaging data is used to guide the pooling strategy of clinical samples for a molecular test.

32 Claims, 8 Drawing Sheets

(51) Int. Cl.
G06T 7/11 (2017.01)
G06K 9/32 (2006.01)
G06F 40/20 (2020.01)
G16H 10/40 (2018.01)
G16H 30/40 (2018.01)
G16H 50/20 (2018.01)
G16H 50/50 (2018.01)
G16H 50/70 (2018.01)
G16H 50/80 (2018.01)
G06T 7/70 (2017.01)
A61B 6/00 (2006.01)
C12Q 1/689 (2018.01)

(52) U.S. Cl.
CPC .......... *C12Q 1/689* (2013.01); *G06F 40/20* (2020.01); *G06K 9/3241* (2013.01); *G06K 9/628* (2013.01); *G06K 9/6256* (2013.01); *G06T 7/11* (2017.01); *G06T 7/70* (2017.01); *G16H 10/40* (2018.01); *G16H 30/40* (2018.01); *G16H 50/20* (2018.01); *G16H 50/50* (2018.01); *G16H 50/70* (2018.01); *G16H 50/80* (2018.01); *G06K 2209/05* (2013.01); *G06T 2207/10116* (2013.01); *G06T 2207/20076* (2013.01); *G06T 2207/20081* (2013.01); *G06T 2207/20084* (2013.01); *G06T 2207/30061* (2013.01)

(58) Field of Classification Search
CPC ........ G16H 50/50; G16H 50/70; G16H 50/80; Y02A 90/10
See application file for complete search history.

(56) References Cited

OTHER PUBLICATIONS

Li et al., "Molecular immune pathogenesis and diagnosis of COVID-19", Journal of Parmaceutical Analysis 10 (2020), pp. 102-108 (Year: 2020).*

Chan et al., "Improved Molecular Diagnosis of COVID-19 by the Novel, Highly Sensitive and Specific COVID-19-RdRp/Hel Real-Time Reverse Transcription-PCR Assay Validated In Vitro and with Clinical Specimens", Journal of Clinical Microbiology, May 2020, vol. 58, Issue 5, pp. 1-10 (Year: 2020).*

Saining Xie, et al., Aggregated residual transformations for deep neural networks, arXiv preprint arXiv:1611.05431, 2016.

Olaf Ronneberger, et al., U-net: Convolutional networks for biomedical image segmentation. Lecture Notes in Computer Science, pp. 234-241 (2015).

Shin, et al., Proceedings of the IEEE Conference on Computer Vision and Pattern Recognition, pp. 2497-2506, 2016.

John Zech, et al., Natural Language-based Machine Learning Models for the Annotation of Clinical Radiology Reports, Radiology (2018).

* cited by examiner

SYSTEMS AND METHODS FOR DETECTION OF INFECTIOUS RESPIRATORY DISEASES

RELATED APPLICATIONS

This application claims priority benefit of Indian Patent Application No. 202021016685, filed Apr. 17, 2020, which are incorporated entirely by reference herein for all purposes.

TECHNICAL FIELD

This disclosure generally pertains to systems and methods for detection of infectious respiratory diseases by implementation of an automated X-ray-based triage approach alongside algorithmic clinical sample pooling for molecular diagnosis.

BACKGROUND ART

Infectious diseases, whether or bacterial, viral, or other origin, present acute and chronic challenges to human health. Many common infections affect the respiratory tract. Respiratory tract diseases, particularly infectious respiratory diseases of viral and bacterial origin, are prevalent in patients of all ages, although often are more serious in the very young and the very old. Viruses include DNA viruses and RNA viruses. Bacteria include Gram positive and Gram negative bacteria, and may include mycoplasma (bacteria lacking cell walls). In addition to disease-causing bacteria, some diseases, such as, e.g., respiratory diseases, may be caused by other microorganisms such as yeasts, fungi, and other small, disease-causing organisms.

An example of a common viral cause of respiratory (and other) disorders in patients is the influenza ("flu") virus. Influenza refers to disease caused by one of several related RNA viruses of the Orthomyxoviridae family, typified by fever, headache, fatigue, and other symptoms. There are different types of influenza; influenza A and influenza B are both about equally prevalent in humans. Identification of the strain of flu in a sample can help suggest treatments, can help suggest preventive measures to be taken, and can help to track such infections in a population.

Another example of viral cause of respiratory disorders in patients is the coronavirus. Numerous coronaviruses, first discovered in domestic poultry in the 1930s, cause respiratory, gastrointestinal, liver, and neurologic diseases in animals. Only 7 coronaviruses are known to cause disease in humans. Three of the 7 coronaviruses cause much more severe, and sometimes fatal, respiratory infections in humans than other coronaviruses and have caused major outbreaks of deadly pneumonia in the 21st century. SARS-CoV2 is a novel coronavirus identified as the cause of coronavirus disease 2019 (COVID-19) that was identified in late 2019 and spread extensively worldwide. MERS-CoV was identified in 2012 as the cause of Middle East respiratory syndrome (MERS). SARS-CoV was identified in 2002 as the cause of an outbreak of severe acute respiratory syndrome (SARS).

Examples of common bacterial causes of respiratory (and other) disorders in patients include whooping cough, pneumonia, and tuberculosis. Whooping cough is caused by *Bordetella pertussis* and is typified by fits of violent coughing, which may persist for weeks. Pneumonia is the name given to respiratory disorders characterized by fluid in the lungs, coughing, fever, vomiting, fatigue, and other symptoms. Pneumonia may be caused by bacterial or viral infection; determination of the cause of a particular case is critical in determining the course of treatment of the patient. Causes of pneumonia include *Streptococcus pneumonia*, *Staphylococcus aureus*, adenovirus, influenza viruses, respiratory syncytial virus, *Pneumocystis, jirovecii* (a fungus), and other agents. Tuberculosis is caused by *Mycobacterium tuberculosis*, is typified by cough including spitting up blood, chest pain, chills, fever, night sweats, and other symptoms, and may be fatal.

Agents that cause infectious respiratory diseases typically differ between upper respiratory tract diseases and lower respiratory tract disorders; thus, the variety or range of bacterial or viral agents found in patients suffering from upper respiratory disorders may be different than those bacterial or viral agents found in patients suffering from lower respiratory disorders. However, successful diagnosis and treatment of respiratory diseases often requires identification of disease-causing organisms present in a clinical sample obtained from a subject suffering, or suspected of suffering, from an infectious respiratory disorder. Differentiating between organisms typical of upper respiratory and those typical of lower respiratory disorders may also be critical in the successful diagnosis and treatment of respiratory diseases. In addition, identification of other symptoms and sequelae of respiratory disorders may aid the successful diagnosis and treatment of respiratory diseases.

In order to be effective in treating such infectious disorders, testing must be timely. However, present methods and systems for testing are often time-consuming, and may be expensive. Methods that require large amounts of sample, or that require incubation of a sample for a day or days, are often ineffective at timely detection or identification of the cause of a respiratory disorder, and thus may not be helpful in the diagnosis or treatment of infectious respiratory disorders.

Thus, improved methods and systems for the detection and identification of agents that cause diseases, such as influenza, respiratory diseases, viral diseases, bacterial diseases, and other diseases, are desired.

SUMMARY OF THE INVENTION

The present invention provides systems and methods for detection of infectious respiratory diseases by implementation of an automated X-ray-based triage approach alongside algorithmic clinical sample pooling for molecular diagnosis. The automated X-ray-based triage approach is based on an automated deep learning system that is trained to detect and localize abnormalities from chest X-ray scans.

In particular, an embodiment provides a method for detection of an infectious respiratory disease by implementation of an automated X-rays-based triage approach alongside algorithmic clinical sample pooling for molecular diagnosis, comprising:

receiving a clinical sample and chest X-ray scan imaging procedure data from a subject;

processing images from the chest X-ray scan imaging procedure data;

detecting and localizing medical abnormalities of the images using a deep learning system, generating a first score that corresponds to a level of recognition of each of the medical abnormalities and outputting a bounding box representing the precise location and extent of the medical abnormalities;

generating a second score for each subject that corresponds to a level of recognition of an infectious respiratory disease based on the first scores of the medical abnormalities that suggest a typical or atypical symptom of the infectious respiratory disease;

mapping the second score to a probability of a subject having the infectious respiratory disease;

ranking the clinical sample of each subject from lowest to highest based on the second score; and selecting a pooling size of clinical samples for a molecular test based on a collective probability of all the subjects having the infectious respiratory disease in a pool, wherein the collective probability is a sum of the probability of each subject having the infectious respiratory disease in the pool and wherein the probability is lesser than or equal to 1.

Another embodiment provides a system for detection of an infectious respiratory disease by implementation of an automated X-rays-based triage approach alongside algorithmic clinical sample pooling for molecular diagnosis, comprises a first subsystem for automating detection and localization of medical abnormalities on chest X-ray imaging scans using a deep learning algorithm carried out by a computer, wherein the deep learning algorithm is developed by the steps of:

receiving and processing images from the chest X-ray scan imaging procedure data;

detecting and localizing medical abnormalities of the images using a deep learning system, wherein the deep learning system carried out by a computer is developed by the steps of:

generating a first score that corresponds to a level of recognition of each of the medical abnormalities and outputting a bounding box representing the precise location and extent of the medical abnormalities; and generating a second score for each subject that corresponds to a level of recognition of an infectious respiratory disease based on the first scores of the medical abnormalities that suggest typical or atypical infectious respiratory disease; and a second subsystem for algorithmic pooling of clinical samples from each subject who also receives chest X-ray scans, wherein the algorithmic pooling is carried out by a computer following the steps of:

mapping the second score derived from the first subsystem to a probability of a subject having the infectious respiratory diseases;

ranking the clinical samples from lowest to highest based on the second score; and selecting a pooling size of the clinical samples for a molecular test based on a collective probability of all the subjects having the infectious respiratory disease in a pool, wherein the collective probability is a sum of the probability of each subject having the infectious respiratory disease in the pool and wherein the probability is lesser than or equal to 1.

According to one embodiment, the deep learning system carried out by a computer for analyzing chest X-ray scans is developed by the steps of:

selecting medical imaging scans and extracting the medical abnormalities using natural language processing (NLP) algorithms to generate extracted findings, wherein the extracted findings are used as labels for training a deep learning algorithm, wherein the medical abnormalities comprise blunted costophrenic angle, calcification, cardiomegaly, cavity, cervical rib, consolidation, hyper inflation, fibrosis, prominence in hilar region, opacity, pleural effusion, and scoliosis;

segmenting, via an anatomy segmenter, the selected chest X-ray imaging scans to generate segmentation masks corresponding to chest cavity, lungs, diaphragm, mediastinum and ribs;

outputting, via a region of interest (ROI) generator, a plurality of ROIs that are relevant for detecting a particular abnormality, wherein the ROI generator uses the chest X-ray imaging scan at full resolution and the corresponding anatomy segmentation masks; and detecting the abnormalities, via abnormality detector, and outputting a low-resolution probability map per each ROI, a confidence score per each ROI, and a confidence score for an entire chest X-ray scan by combining the confidence scores per each ROI, wherein the abnormality detector is a hybrid classification plus segmentation network.

According to a further embodiment, the extracted findings comprise locations, severity, size, shape and texture. The labels comprise scan-level labels, ROI level labels and pixel level labels.

According to another embodiment, the NLP algorithms are rule-based. The deep learning algorithm comprises convolutional neural networks (CNNs).

In at least one embodiment, the anatomy segmenter uses a U-Net based neural network. The ROI generator is rule-based. The abnormality detector is based on ResNeXT-50 with Squeeze-excitation modules (SE-ResNeXT-50).

In at least one embodiment, the deep learning system uses a weighted sum of cross entropy loss at three levels comprising ROI level predictions, pixel level probability maps, and final pooled chest X-ray scan level prediction. The confidence scores per each ROI are combined using a pooling operator that is a convex approximation of LogSum-Exp (LSE) function.

In at least one embodiment, the infectious respiratory disease is a bacterial disease, or a viral disease, or another type of disease, and the analysis of the clinical sample determines whether the infectious disease is a bacterial disease, a viral disease, or another type of disease. The determination of the type of infectious respiratory disease aids in determining the type of treatment to provide to the subject, e.g., where the determination indicates the infectious disease is a viral disease, the subject should be treated with antiviral drugs; where the determination indicates the infectious disease is a bacterial disease, the subject should be treated with antibiotics drugs; where the determination indicates the infectious disease is a fungal disease, the subject should be treated with anti-fungal drugs; where the determination indicates the infectious disease is a yeast infection, the subject should be treated with anti-yeast drugs; and so forth.

In at least one embodiment, The infectious respiratory diseases include, but is not limited to, tuberculosis, pertussis, Swine influenza (H1N1), Avian influenza (H5N1), Enterovirus infectious diseases, Influenza A, Influenza B, Bronchitis, Coronavius COVID-19 (SARS-CoV-2), Severe Acute Respiratory Syndrome (SARS), and Middle East Respiratory Syndrome (MERS).

In at least one embodiment, the molecular diagnosis comprises detecting the presence of a nucleic acid disease marker and a protein disease marker.

In at least one embodiment, the clinical sample is a sputum sample.

In at least one embodiment, a disease marker is a marker for a disease-causing agent, wherein said disease-causing agent is selected from the group of disease-causing organisms consisting of a virus, a bacterium, a mycoplasm, a fungus, a yeast, and other micro-organisms. In embodiments, a disease marker for a disease-causing agent is selected from the group consisting of Influenza A Matrix protein, Influenza H3N2, Influenza H1N1 seasonal, Influenza H1N1 novel, Influenza B, *Streptococcus pyogenes* (A), *Mycobacterium Tuberculosis*, Rifampin, *Staphylococcus aureus* (MR), *Staphylococcus aureus* (RS), *Bordetella pertussis* (whooping cough), *Streptococcus agalactiae* (B), Influenza H5N1, Influenza H7N9, Epstein Barr Virus (mono), Rhinovirus, Parainfluenza virus (1), Parainfluenza virus (2), Parainfluenza virus (3), Parainfluenza virus (4a), Parainfluenza virus (4b), Respiratory syncytial virus (RSV) A, Respiratory syncytial virus (RSV) B, Coronavirus 229E, Coronavirus HKU1, Coronavirus OC43, Coronavirus NL63, Novel Coronavirus COVID-19, Bocavirus, human metapneumovirus (HMPV), *Streptococcus pneumoniae* (penic R), *Streptococcus pneumoniae* (S), *Mycoplasma pneumoniae, Chlamydia pneumoniae, Bordetella parpertussis, Haemophilus influenzae* (ampic R), *Haemophilus influenzae* (ampic S), *Moraxella catarrhalis, Pseudomonas* spp (*aeruginosa*), *Haemophilus parainfluenzae, Enterobacter cloacae* (Enterobacteriaceae spp), *Enterobacter aerogenes* (Enterobacteriaceae spp), *Serratia marcescens* (Enterobacteriaceae spp), and *Legionella* spp.

BRIEF DESCRIPTION OF DRAWINGS

The invention will be described in more detail below on the basis of a drawing, which illustrates exemplary embodiments. In the drawing, in each case schematically.

DETAILED DESCRIPTION

Figure 1:
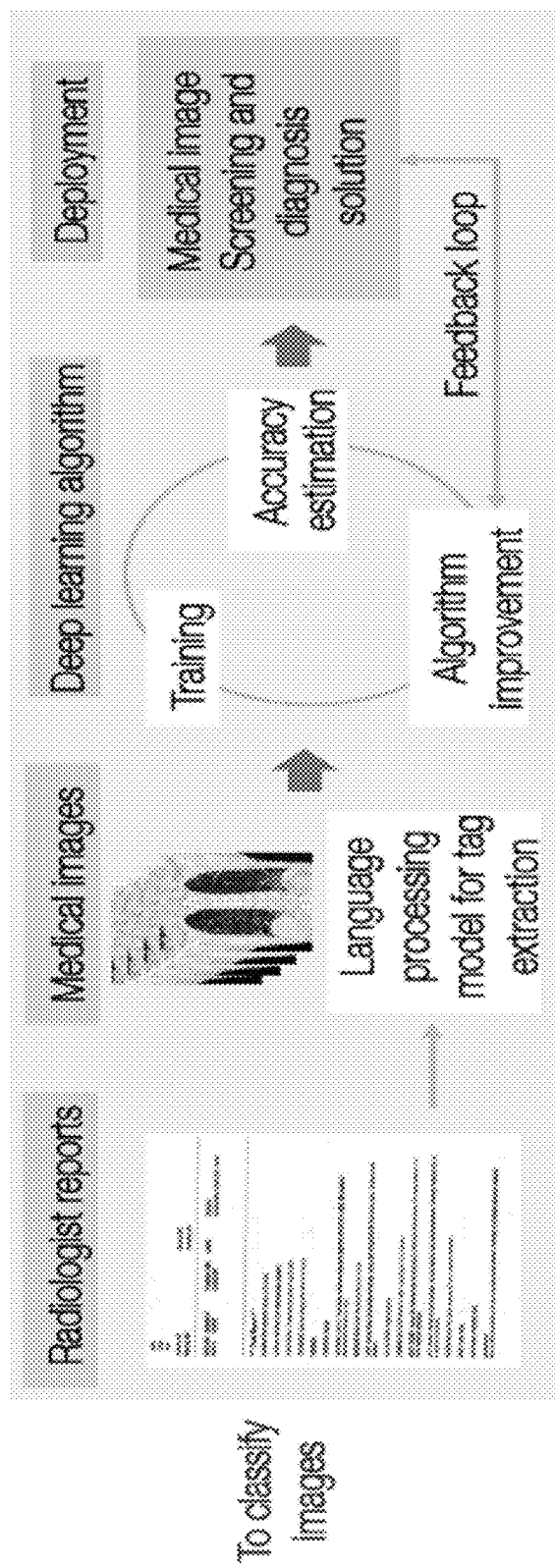
FIG. 1 An exemplary workflow of the deep learning system.

It should be understood that this invention is not limited to the particular methodology, protocols, and systems, etc., described herein and as such may vary. The terminology used herein is for the purpose of describing particular embodiments only, and is not intended to limit the scope of the present invention, which is defined solely by the claims.

As used in the specification and appended claims, unless specified to the contrary, the following terms have the meaning indicated below.

"Architecture" refers to a set of rules and methods that describe the functionality, organization, and implementation of computer systems.

"Convolutional neural network (CNN)" refers to a class of deep, feed-forward artificial neural networks, most commonly applied to analyzing visual imagery. CNNs use a variation of multilayer perceptrons designed to require minimal preprocessing. A CNN consists of an input and an output layer, as well as multiple hidden layers. The hidden layers of a CNN typically consist of convolutional layers, pooling layers, fully connected layers and normalization layers. Convolutional layers apply a convolution operation to the input, passing the result to the next layer. Local or global pooling layers combine the outputs of neuron clusters at one layer into a single neuron in the next layer. Fully connected layers connect every neuron in one layer to every neuron in another layer. CNNs use relatively little pre-processing compared to other image classification algorithms. This means that the network learns the filters that in traditional algorithms were hand-engineered. This independence from prior knowledge and human effort in feature design is a major advantage.

"Heuristics" refers to a technique designed for solving a problem more quickly when classic methods are too slow, or for finding an approximate solution when classic methods fail to find any exact solution. This is achieved by trading optimality, completeness, accuracy, or precision for speed. In a way, it can be considered a shortcut. A heuristic function, also called simply a heuristic, is a function that ranks alternatives in search algorithms at each branching step based on available information to decide which branch to follow. The objective of a heuristic is to produce a solution in a reasonable time frame that is good enough for solving the problem at hand. This solution may not be the best of all the solutions to this problem, or it may simply approximate the exact solution.

"Natural Language Processing (NLP)" refers to a way for computers to analyze, understand, and derive meaning from human language in a smart and useful way. By utilizing NLP, developers can organize and structure knowledge to perform tasks such as automatic summarization, translation named entity recognition, relationship extraction, sentiment analysis, speech recognition, and topic segmentation.

"LogSumExp (LSE) function" refers to a smooth maximum: a smooth approximation to the maximum function, mainly used by machine learning algorithms. See Nielsen, Frank, et. al., Guaranteed bounds on the Kullback-Leibler divergence of univariate mixtures using piecewise log-sum-exp inequalities, Entropy. 2016.

"Cross entropy loss" measures the performance of a classification model whose output is a probability value between 0 and 1. Cross-entropy loss increases as the predicted probability diverges from the actual label. So predicting a probability of 0.012 when the actual observation label is 1 would be bad and result in a high loss value. A perfect model would have a log loss of 0.

The present disclosure illustrates various techniques and configurations that enable the integration and use of machine learning analysis in a data-driven image evaluation workflow. For example, machine learning analysis (such as trained models of image detection of certain medical conditions) may be performed upon medical imaging procedure data produced as part of a medical imaging study. The medical imaging procedure data may include image data captured by an imaging modality, and order data (such as data indicating a request for a radiological image read), each produced to facilitate a medical imaging evaluation (such as a radiology read to be performed by a radiologist or a diagnostic evaluation by another qualified medical professional).

For example, the machine learning analysis may receive and process images from medical imaging procedure data, to identify trained structures, conditions, and conditions within images of a particular study. The machine learning analysis may result in the automated detection, indication, or confirmation of certain medical conditions within the images, such as the detection of urgent or life-critical medical conditions, clinically serious abnormalities, and other key findings. Based on the result of the machine learning analysis, the medical evaluation for the images and the associated imaging procedure may be prioritized, or otherwise changed or modified. Further, the detection of the medical conditions may be used to assist the assignment of the medical imaging data to particular evaluators, the evaluation process for the medical imaging data, or implement other actions prior to, or concurrent with, the medical imaging evaluation (or the generation of a data item such as a report from such medical imaging evaluation).

As further discussed herein, the machine learning analysis may be provided on behalf of any number of machine learning algorithms and trained models, including but not limited to deep learning models (also known as deep machine learning, or hierarchical models) that have been trained to perform image recognition tasks, particularly for certain types of medical conditions upon medical images of human anatomy and anatomical representations. As used herein, the term "machine learning" is used to refer to the various classes of artificial intelligence algorithms and algorithm-driven approaches that are capable of performing machine-driven (e.g., computer-aided) identification of trained structures, with the term "deep learning" referring to a multiple-level operation of such machine learning algorithms using multiple levels of representation and abstraction. However, it will be apparent that the role of the machine learning algorithms that are applied, used, and configured in the presently described medical imaging evaluation may be supplemented or substituted by any number of other algorithm-based approaches, including variations of artificial neural networks, learning-capable algorithms, trainable object classifications, and other artificial intelligence processing techniques.

In some of the following examples, reference is made to radiology medical imaging procedures (e.g., computed tomography (CT), magnetic resonance imaging (MRI), Ultrasound, and X-ray procedures, etc.) and diagnostic evaluation of the images produced from such imaging procedures that would be performed with an image evaluation (e.g., radiology read) by a licensed and credentialed radiologist. It will be understood that the applicability of the presently described techniques and systems will extend to a wide variety of imaging data (and other data representations) produced by various medical procedures and specialties, including those not involving traditional radiology imaging modalities. Such specialties include, but are not limited, to pathology, medical photography, medical data measurements such as electroencephalography (EEG) and electrocardiography (EKG) procedures, cardiology data, neuroscience data, preclinical imaging, and other data collection procedures occurring in connection with telemedicine, telepathology, remote diagnostics, and other applications of medical procedures and medical science. Accordingly, the performance of the data recognition and workflow modification techniques described herein may apply to a variety of medical image data types, settings, and use cases, including captured static images and multi-image (e.g. video) representations.

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments.

An embodiment provides a method for detection of infectious respiratory diseases by implementation of an automated X-rays-based triage approach alongside algorithmic clinical sample pooling for molecular diagnosis, comprising:
  receiving a clinical sample and chest X-ray scan imaging procedure data from a subject;
  processing images from the chest X-ray scan imaging procedure data;
  detecting and localizing medical abnormalities of the images using a deep learning system,
  generating a first score that corresponds to a level of recognition of each of the medical abnormalities and outputting a bounding box representing the precise location and extent of the medical abnormalities;
  generating a second score for each subject that corresponds to a level of recognition of an infectious respiratory disease based on the first scores of the medical abnormalities that suggest a typical or atypical symptom of the infectious respiratory disease;
  mapping the second score to a probability of a subject having the infectious respiratory disease;
  ranking the clinical sample from lowest to highest based on the second score; and
  selecting a pooling size of the clinical sample for a molecular test based on a collective probability of all the subjects having the infectious respiratory disease in a pool, wherein the collective probability is a sum of the probability of each subject having the infectious respiratory disease in the pool and wherein the probability is lesser than or equal to 1.

Another embodiment provides a system for detection of infectious respiratory diseases by implementation of an automated X-rays-based triage approach alongside algorithmic clinical sample pooling for molecular diagnosis, comprises
  a first subsystem for automating detection and localization of medical abnormalities on chest X-ray imaging scans using a deep learning algorithm carried out by a computer, wherein the deep learning algorithm is developed by the steps of:
    receiving and processing images from the chest X-ray scan imaging procedure data;
    detecting and localizing medical abnormalities of the images using a deep learning system, wherein the deep learning system carried out by a computer is developed by the steps of:
    generating a first score that corresponds to a level of recognition of each of the medical abnormalities and outputting a bounding box representing the precise location and extent of the medical abnormalities; and
    generating a second score for each subject that corresponds to a level of recognition of an infectious respiratory disease based on the first scores of the medical abnormalities that suggest typical or atypical infectious respiratory disease; and
  a second subsystem for algorithmic pooling of clinical samples from the subject who also receives chest X-ray scans, wherein the algorithmic pooling is carried out by a computer following the steps of:
    mapping the second score derived from the first subsystem to a probability of a subject having the infectious respiratory diseases;
    ranking the clinical sample from lowest to highest based on the second score; and
    selecting a pooling size of the clinical sample for a molecular test based on a collective probability of all the subjects having the infectious respiratory disease in a pool, wherein the collective probability is a sum of the probability of each subject having the infectious respiratory disease in the pool and wherein the probability is lesser than or equal to 1.

FIG. 1 illustrates the exemplary workflow of the first subsystem for automating detection and localization of medical abnormalities on chest X-ray imaging scans using a deep learning algorithm. More than 2.5 millions chest X-Ray scans and their corresponding radiology reports were used to train convolutional neural networks (CNNs) to identify the abnormalities. The X-ray scans together with the radiology reports are collectively called imaging procedure data. Natural language processing (NLP) algorithms were developed to parse unstructured radiology reports and extract information about the presence of abnormalities in the chest X-ray scans. These extracted findings were used as labels when training CNNs. The extracted findings comprise locations, severity, size, shape and texture. The labels comprise scan-level labels, ROI level labels and pixel level labels. See U.S. patent application Ser. No. 16/798,544, which is incorporated entirely by reference herein for all purposes.

The NLP algorithm was constructed using a thoracic imaging glossary, curated by a panel of radiologists and tailored to be consistent with the predefined abnormality definitions. This algorithm is rule-based as opposed to machine-learning based NLP. See John Zech, et. al., Natural Language-based Machine Learning Models for the Annotation of Clinical Radiology Reports, Radiology (2018). Rule-based systems performed better than learned methods, probably because of the vast amount of domain specific knowledge that had to be imparted which would require large amounts of annotated data. The proprietary NLP algorithm is essentially a large set of rules.

Since data was collected from multiple sources, the reporting standards were not consistent. The same finding can be noted in several different formats. For example, the finding Blunted Costophrenic angle can be reported in either of the following ways: "CP angle is obliterated"; "Hazy costophrenic angles"; or "Obscured CP angle". The system collected all the wordings that can be used to report findings and created a rule for each finding.

The rule would be positive if there are words angle and blunted or their synonyms in a sentence. In addition to such rules, there can be hierarchical structure in findings. For example, opacity is considered positive if any of edema, consolidation, groundglass, etc. are positive. The system therefore created a ontology of findings and rules to deal with this hierarchy.

In addition to these rules that pick mentions of abnormal findings from reports, to obtain the final labels, the system performs negation detection, uncertainty detection and a set of standard NLP techniques to account for formatting and grammatical issues. The system also extracts qualifiers like left, right, upper zone, etc. that serve as additional labels for a given image. The final algorithm is validated by expert radiologists. A group of 5 experts were given the abnormality definitions. A dataset of 1930 reports along with their chest X-rays were presented to this group and the findings extracted by the NLP algorithm were compared against the findings extracted by the experts. Results from this validation are presented in the main text.

Table 1 lists definitions that were used when extracting radiological findings from the reports.

TABLE 1

| | Abnormality definitions | |
|---|---|---|
| Finding | Definition for tag extraction from radiology reports | Definition for radiologist review |
| Normal | 'No abnormality detected' or 'Normal' | Normal X-ray |
| Blunted CP angle | Blunted CP angle | CP Angle blunted or obscured. Could be due to pleural effusion or pleural thickening |
| Calcification | Calcification | All calcifications on X-ray including but not limited to aortic arch calcification, rib calcifications, calcified pulmonary densities and microcalcifications |
| Cardiomegaly | Cardiomegaly | Cardiothoracic ratio >0.5 |
| Cavity | Pulmonary cavity | Pulmonary cavity |
| Consolidation | Consolidation, pneumonia or air-bronchogram | Pulmonary consolidation |
| Fibrosis | Fibrosis | Any evidence of lung fibrosis, including interstitial fibrosis, fibrocavitary lesion |
| Hilar prominence | Hilar enlargement, prominent hilum or hilar lymphadenopathy | Enlarged or prominent hilum or including hilar lymphadenopathy |
| Opacity | Any lung field opacity or opacities, shadow or density including but not limited to infiltrate, consolidation, mass, nodule, pulmonary calcification, and fibrosis | Any lung field opacity or multiple opacities including but not limited to infiltrate, consolidation, mass, nodule, pulmonary calcification, and fibrosis. Pleural abnormalities not included under this tag |
| Pleural Effusion | Pleural Effusion | Pleural Effusion |

These findings are referred as tags. Tag extraction accuracy was measured versus a set of reports where abnormalities were manually extracted. Tag extraction accuracy was reported in Table 2.

TABLE 2

Tag extraction accuracy.

| Finding | #Positives | Sensitivity (95% CI) | Specificity (95% CI) |
|---|---|---|---|
| Normal (No abnormality detected) | 105 | 0.9429 (0.8798-0.9787) | 1.0000 (0.9959-1.0000) |
| Blunted CP angle | 146 | 0.9795 (0.9411-0.9957) | 0.9824 (0.9712-0.9901) |
| Calcification | 116 | 1.0000 (0.9687-1.0000) | 0.9660 (0.9519-0.9770) |
| Cardiomegaly | 125 | 0.9920 (0.9562-0.9998) | 0.9760 (0.9635-0.9851) |
| Cavity | 30 | 1.0000 (0.8843-1.0000) | 0.9856 (0.9759-0.9921) |
| Consolidation | 161 | 0.9876 (0.9558-0.9985) | 0.9761 (0.9634-0.9854) |
| Fibrosis | 124 | 0.9839 (0.9430-0.9980) | 0.9931 (0.9851-0.9975) |
| Hilar Enlargement | 289 | 0.9689 (0.9417-0.9857) | 0.9732 (0.9585-0.9838) |
| Opacity | 612 | 0.9608 (0.9422-0.9747) | 0.9251 (0.8942-0.9492) |
| Pleural Effusion | 246 | 0.9309 (0.8917-0.9592) | 0.9602 (0.9436-0.9730) |
| Total (all findings) | 1954 | 0.9672 (0.9584-0.9747) | 0.9771 (0.9736-0.9803) |

Figure 2:
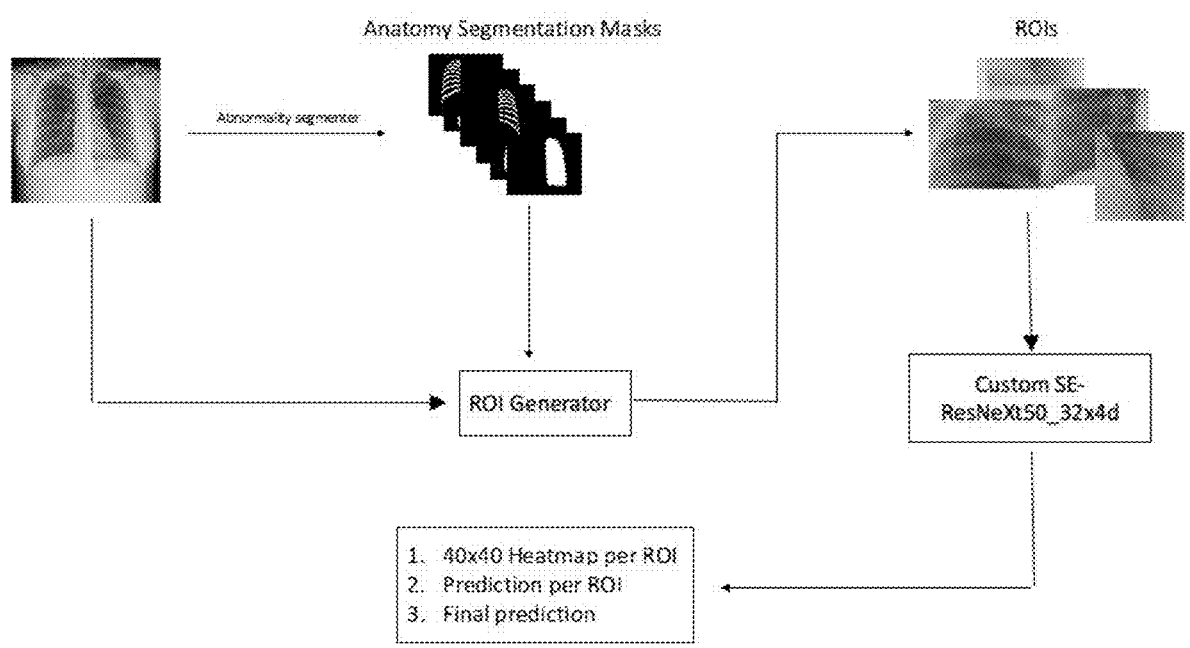
FIG. 2 An exemplary workflow of abnormality detection

The next step is to train the deep learning system for abnormality detection. The optimal deep learning algorithm architecture differs based on the abnormality being detected, hence separate detection algorithms for each abnormality are trained. A particular abnormality detection pipeline comprises: anatomy segmenter, Region of Interest (ROI) generator, and abnormality detector. See. FIG. 2. Given a chest X-ray, the anatomy segmenter outputs segmentation maps to extract lungs, diaphragm, mediastinum and ribs. The ROI generator uses the chest X-ray at full resolution and the corresponding anatomy segmentation masks to output a set of ROIs that are most relevant for detecting a particular abnormality. The abnormality detector is a hybrid classification plus segmentation network that uses the above set of ROIs. The abnormality detector produces outputs including a low-resolution probability map per ROI, a list of confidence scores, one per ROI, and a confidence score for the entire chest X-ray exam by combining the list of per ROI confidence scores.

To build the anatomy segmenter, a set of 5000 chest X-rays were annotated at the pixel level with each of the above anatomical labels. A U-Net based neural network was trained to output anatomical segmentation masks corresponding to the lungs, diaphragm, mediastinum and ribs. See Olaf Ronneberger, et. al., U-net: Convolutional networks for biomedical image segmentation. Lecture Notes in Computer Science, pages 234-241 (2015). These segmentation networks operate on 256×256 resized versions of the chest X-ray.

The ROI generator module is completely rule-based and is developed in close collaboration with radiologists. The output of this module varies depending on the abnormality detected. As an example, for pleural effusion, this module generates two ROIs that cover the lower halves of the lung along with the costophrenic angles and a part of the diaphragm. For lung parenchymal abnormalities, the ROI generator outputs ROIs that together cover the lungs from apex to the diaphragm. For cardiomegaly, the ROI generated is a single image of the entire chest X-ray resized to 320×320 pixels. Each of these ROIs are then resized to a standard size of 320×320 pixels before being fed into the abnormality detector. Before the ROIs are generated, the original chest X-ray is resized to 2000×2000 pixels.

The use of ROI generator to filter out regions in the x-ray that are not essential for a particular abnormality detection model enables the use of significantly higher resolution for the final classification networks. For example, the pleural effusion detection model sees the costophrenic angles and other relevant anatomy at a resolution that is significantly higher than a model that uses the entire chest X-ray as input.

The abnormality detector is based on ResNeXT-50 with Squeeze-excitation modules (SE-ResNeXT-50). See Saining Xie, et. al., Aggregated residual transformations for deep neural networks, arXiv preprint arXiv:1611.05431, 2016. These modules are modified to operate on images that are significantly larger and use multiple types of labels (hybrid) during training. This module operates on the set of ROIs (320×320 pixels) generated and outputs a probability map (40×40 pixels) and a confidence score per ROI. These per ROI confidence scores are combined using a pooling operator that is a convex approximation of the max function, for example, the LogSumExp (LSE) function.

The proprietary deep learning system uses a weighted sum of cross entropy loss at 3 levels comprising on the ROI level predictions; on the pixel level probability maps; and on the final pooled chest X-ray exam level prediction. The weights for each of the losses were hyper-parameters that were tuned while training.

Chest X-ray level labels for a particular abnormality were available for the entire dataset via the NLP labeler. Labels at other levels were not available for the entire dataset.

The ground truths for ROI level predictions are a combination of expert annotations and NLP generated labels where possible. For example, in a case of a chest X-ray with pleural effusion, the reporting radiologist generally mentions either left, right or bilateral while reporting the abnormality. Since, these qualifications are extracted by NLP algorithms while parsing the reports, it enabled to label ROIs in a scalable fashion. The percentage of abnormal X-ray scans which NLP algorithms were able to label the ROIs ranged from 25-60% across abnormalities. The ROIs from X-ray scans that were reported as normal by the reporting radiologist were labelled automatically as not containing that particular abnormality.

The ground truths for pixel-level probability maps are free-hand annotations done by experts using a custom annotation portal. This is done for approximately 20% of all the abnormal scans (~6% of the entire dataset).

ROI level loss and pixel level loss were set to 0 wherever labels were unavailable. All image ROIs were normalized to have pixel values between 0 and 1 before being presented to the network. Our data augmentation strategy consisted of random crops, brightness, contrast, gamma augmentations and a set of abnormality specific augmentations. See Kaiming He, et. al., Deep residual learning for image recognition, In Proceedings of the IEEE conference on computer vision and pattern recognition, 2016. The aim of data augmentation is to train networks that are unaffected by variability in X-ray machine manufacturer, model, voltage, exposure and other parameters that vary from center to center. Training was done on NVIDIA GPUs using the pytorch framework. Multiple models were trained by varying the model initialization conditions and the distribution of the training dataset and a simple majority scheme is used to combine these models.

When the chest X-ray level prediction is positive for a particular abnormality, all the ROIs that are above a certain threshold are drawn as bounding boxes on the original X-ray for the purpose of highlighting the region responsible for the positive X-ray level prediction. In addition to this, for subtle and small abnormalities like nodule, the 40×40 probability map is thresholded and resized to 320×320 and overlaid on the positive ROI. Visualization is not generated for cardiomegaly as it is a single ROI.

The proprietary system uses an operating point where sensitivity is closest to 0.95. with specificity >0. Otherwise, the system use an operating point where sensitivity is just above 0.90 if available, else the closest to 0.90.

The proprietary deep learning system for automating detection of medical abnormalities on chest X-ray scans particularly address the problem on scalability, sparsity, generalizability.

Annotation is generally limited by the time and expert effort required to label. This system uses a hybrid model for annotation: for a small part of the dataset, annotation is made at pixel, slice and boxes levels; for other images, annotation is made at the scan level where expect annotations are unavailable. Based on the types of labels available, the system uses multi-pronged supervised learning algorithms to define a feature type as an abnormality.

Convolutional layers in a convolutional neural network (CNN) summarize the presence of features in an input image. Pooling layers provide an approach to down sampling feature maps by summarizing the presence of features in patches of the feature map. Two common pooling methods are average pooling and max pooling that summarize the average presence of a feature and the most activated presence of a feature respectively. To solve the sparsity problems, the system use a softmax pooling method that is between average and max pooling.

To address generalizability, the system removes irrelevant parts of the image and increase variance in the dataset artificially by adjusting brightness, contrast, gamma correction, random crop, or scale.

Figure 3:
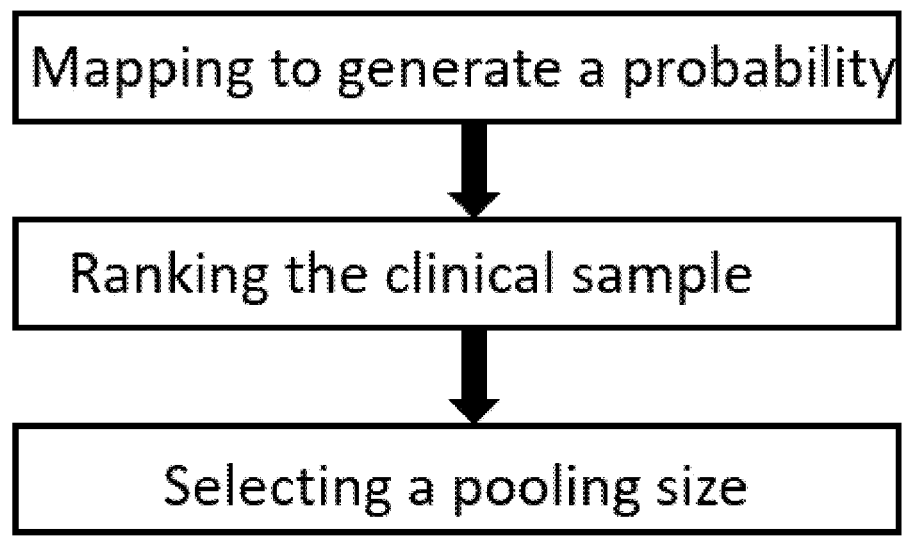
FIG. 3 An exemplary workflow of the second subsystem.

FIG. 3 illustrates the exemplary workflow of the second subsystem for algorithmic pooling of clinical samples from the subject who also receives chest X-ray scans, wherein the algorithmic pooling is carried out by a computer.

The output score generated by the first subsystem is representative of how many of, or how obvious, these signs of abnormal findings, such as Consolidation, Fibrosis, etc, are present in the X-ray scan. However, this output score is not necessarily the probability that a subject is positive for a certain infectious respiratory disease. While the score and the disease probability are proportional, the relationship is not linear, which is highly dependent on the disease prevalence in the specific area. To determine the probability that a subject is positive for a certain infectious respiratory disease, the output score of each subject is mapped to the probability of a subject having a certain infectious respiratory disease based on the demographic prevalence data and/or retrospective data. This relationship between prevalence and the mapping is modeled using a polynomial function where the exponent decreases as the prevalence increases.

The second subsystem maps the output score for each subject generated by the first subsystem that corresponds to a level of recognition of an infectious respiratory disease to a probability of a subject having the infectious respiratory diseases. The mapping curve is generated based on the demographic prevalence data and/or retrospective data.

The second subsystem then ranks the clinical sample from lowest to highest based on the output score; and select a pooling size of the clinical sample for a molecular test based on a collective probability of all the subjects having the infectious respiratory disease in a pool, wherein the collective probability is a sum of the probability of each subject having the infectious respiratory disease in the pool and wherein the probability is lesser than or equal to 1.

EXAMPLES

Example 1. Deep Learning Solution for Tuberculosis Detection

Tuberculosis (TB) is a global public health problem, with the highest burden occurring in low-income countries. In these countries, the use of more sensitive molecular tests, such as Xpert MTB/RIF (Xpert), is still limited by costs. The Xpert assay is a self-contained, fully automated, real-time PCR assay that facilitates rapid semiquantitative detection of *Mycobacterium tuberculosis* (MTB) and rifampin (RIF) resistance with minimal laboratory requirements compared to those needed for culture and other manually operated nucleic acid amplification tests (NAATs).

One approach that can reduce costs is to pool specimens (sputum samples) from several patients and test them using a single test. If a pool tests positive, then each specimen is tested individually to detect the positive sample(s), whereas the pooled specimens test negative, all individuals are considered infection free. The cost savings of pooled testing are determined by the prevalence of disease in the tested population, the number of samples per pool, and the degree of clustering of positive individuals in the tested population.

Current strategy for pooling sputum samples is mainly randomly selection. For example, in one published study, sputum samples from four consecutive patients were pooled and tested using a single Xpert cartridge with follow-on individual testing of positive pools. See Saddiq T, *Testing Pooled Sputum with Xpert MTB/RIF for Diagnosis of Pulmonary Tuberculosis To Increase Affordability in Low-Income Countries*, J. of Clinical Microbiology (2015). Random pooling without knowledge of the samples remains less ideal.

Medical imaging techniques, such as X-ray imaging, are widely used in diagnosis, clinical studies and treatment planning. Due to their affordability, chest X-ray scans are used all over the world. In many parts of the world, the availability of digital chest X-ray machines is growing more rapidly than the availability of clinicians who are trained highly enough to perform this complex task. If automated detection can be applied in low-resource settings as a disease screening tool, the benefits to population health outcomes globally could be significant. One example of such use of chest X-ray is in tuberculosis screening. An effective methodology to optimized the pooling size based on the X-ray screening prior to tuberculosis Xpert diagnostic testing could be useful in helping to guide policy.

Figure 4:
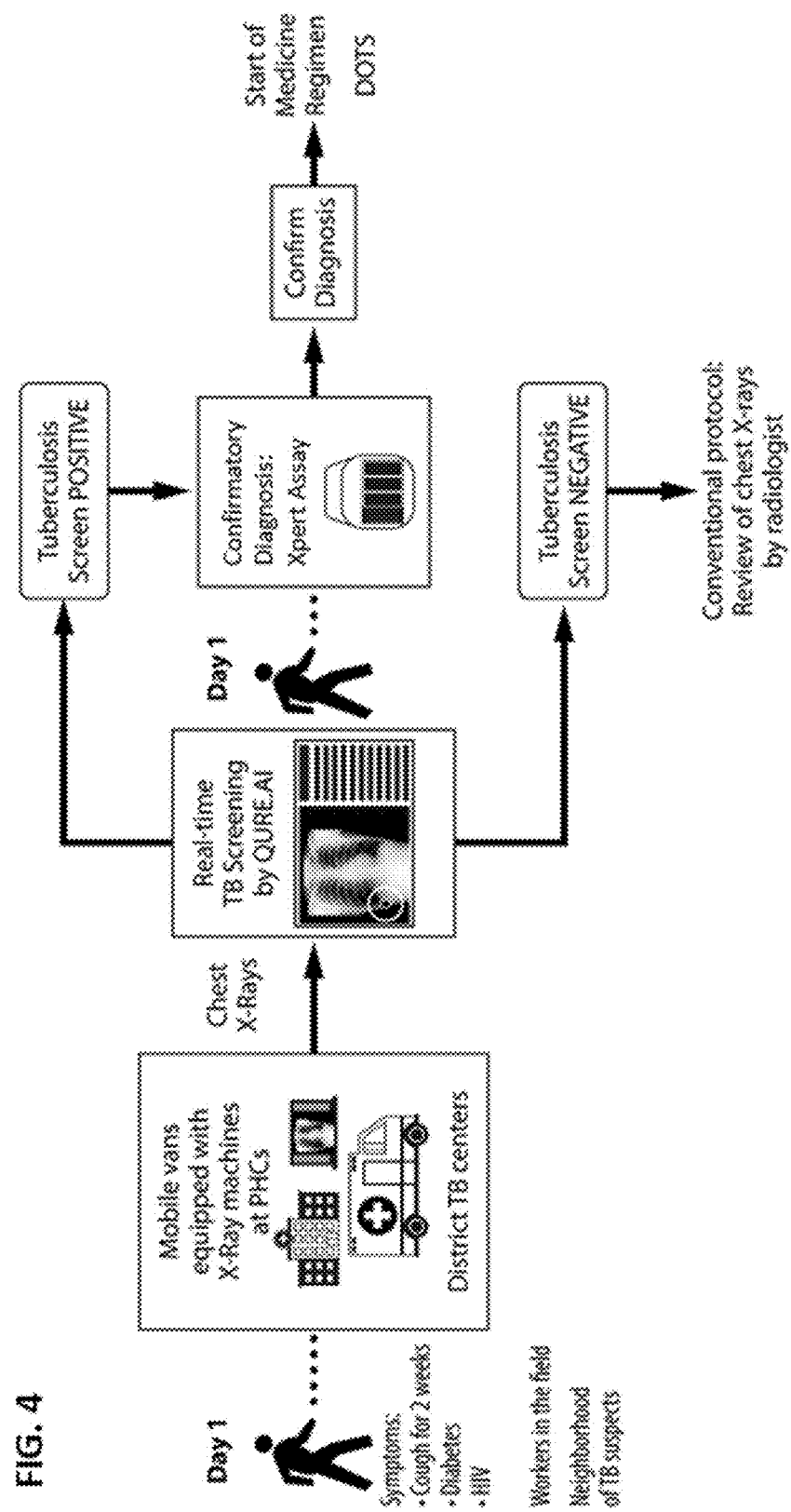
FIG. 4 An exemplary workflow for workflow of the system and method of implementation of an automated X-ray-based triage approach alongside algorithmic sputum pooling for TB molecular diagnosis FIG. 5 An exemplary workflow of generated a TB score.

FIG. 4 illustrates an exemplary workflow of the system and method of implementation of an automated X-ray-based triage approach alongside algorithmic sputum pooling for TB molecular diagnosis. The system is to triage patients for confirmatory testing by Xpert based on X-ray scans. The system comprise a first subsystem for automating detection and localization of medical abnormalities on chest X-ray imaging scans using a deep learning algorithm carried out by a computer; and a second subsystem for algorithmic pooling of sputum samples from the subject who also receives chest X-ray scans.

The system seamlessly integrates with Vendor Neutral Archives (VNA) and PACS without interfering with the existing Radiology workflow. It is deployed in HIPAA compliant cloud servers to deliver a table of results containing:

a. "Normal" or "abnormal" for each chest X-ray b. List of all abnormalities detected by the algorithm with its corresponding probability scores.

c. "Tuberculosis screen advised" or "tuberculosis screen negative" for each X-ray, with probability scores.

Using standard imaging protocols, the system automatically uploads the X-rays of interest (anonymized) from the client PACS/VNA and responds back with the results overlay and corresponding reports using HL7 formats, allowing the user to have access to analysis prior to review of original X-rays. This standard process, ensures that individuals with symptoms like cough over two weeks, diabetes and other immunocompromised patients get their screening for Tuberculosis done within seconds, referred for microbiological confirmation, such as Xpert test, and if found positive, the treatment can start the same day.

The deployment efforts will involve integrating with current X-ray system through an API. The results are compatible with any radiology viewer or can be hosted on a web-based the system viewer.

The algorithm automatically identifies 15 most common chest X-ray abnormalities. A subset of these abnormalities that suggest typical or atypical pulmonary Tuberculosis are combined to generate a "Tuberculosis screening" algorithm within the product. The tuberculosis screening algorithm is intended to replicate a radiologist or physician's screen of chest X-rays for abnormalities suggestive of Tuberculosis, before microbiological confirmation. The system integrates with Vendor Neutral Integration Process and works with X-rays generated from any X-ray system (CR or DR). The system screens for Tuberculosis and also identifies 15 other abnormalities, so that patients can be informed about non-TB conditions they might be suffering from.

Figure 5:
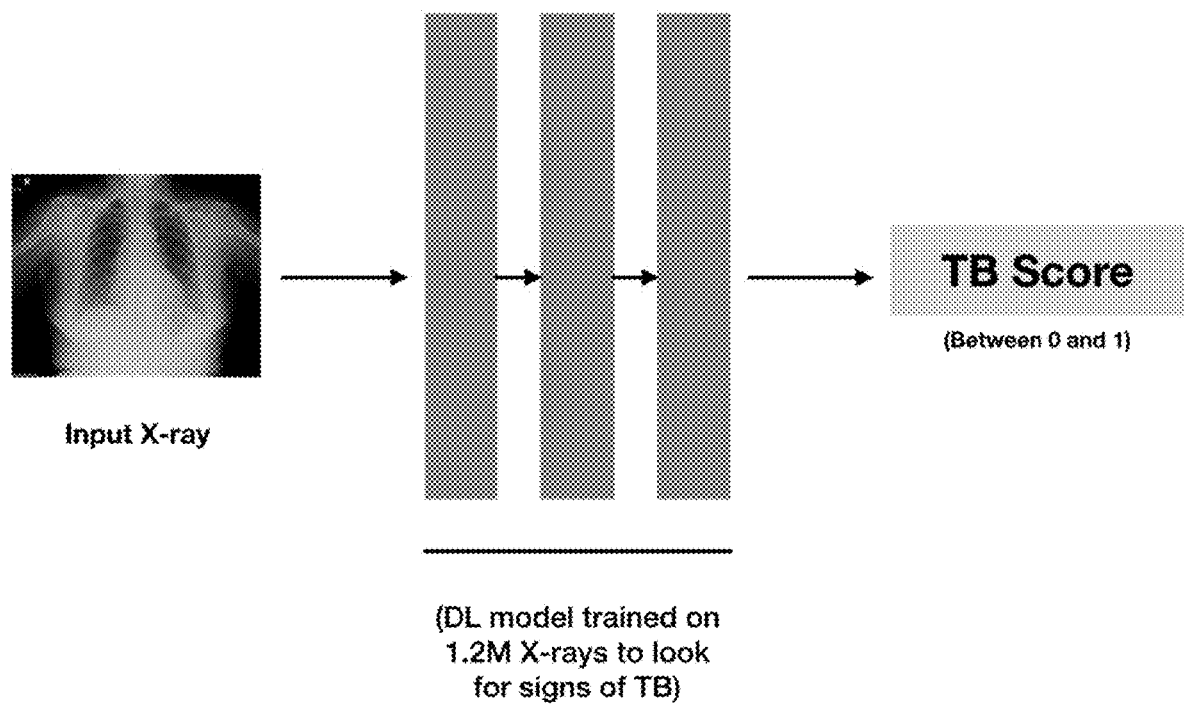

The automated report is created with scores that correspond to a level of recognition of the characteristics of the particular medical condition in the image data. As shown in FIG. 5, a TB score that corresponds to a level of recognition of tuberculosis is generated based on the scores of the medical abnormalities that suggest typical or atypical tuberculosis. Table 3 is an example of the automated report.

TABLE 3

An example of the automated report.
Chest X-Ray abnormality detection and scoring

| X-Ray Findings | Probability | Remark |
| --- | --- | --- |
| Abnormal | 0.94 | YES |
| Blunted Costophrenic angle | 0.24 | NO |
| Calcification | 0.78 | YES |
| Cardiomegaly | 0.11 | NO |
| Cavity | 0.85 | YES |
| Cervical Rib | 0.42 | NO |
| Consolidation | 0.92 | YES |
| Hyper Inflation | 0.44 | NO |
| Fibrosis | 0.8 | YES |
| Prominence in Hilar region | 0.91 | YES |

TABLE 3-continued

An example of the automated report.
Chest X-Ray abnormality detection and scoring

| X-Ray Findings | Probability | Remark |
| --- | --- | --- |
| Opacity | 0.95 | YES |
| Pleural Effusion | 0.08 | NO |
| Scoliosis | 0.1 | NO |
| Tuberculosis screen | 0.96 | ADVISED |

The output TB score generated by the deep learning system is representative of how many of, or how obvious, these signs of abnormal findings, such as Consolidation, Fibrosis, etc, are present in the X-ray scan. However, the TB score is not necessarily the probability that a subject is positive for TB.

While the TB score and the TB probability are proportional, the relationship is not linear, which is highly dependent on the TB prevalence in the specific area. In an area with a low prevalence of TB, like the US or Europe, most of the characteristic signs of TB need to be present in an X-ray to have a higher TB probability. While in countries like India, Africa or other third world countries in general, where TB prevalence is very high, even minimal signs of TB in an X-ray need to be taken seriously.

Figure 6:
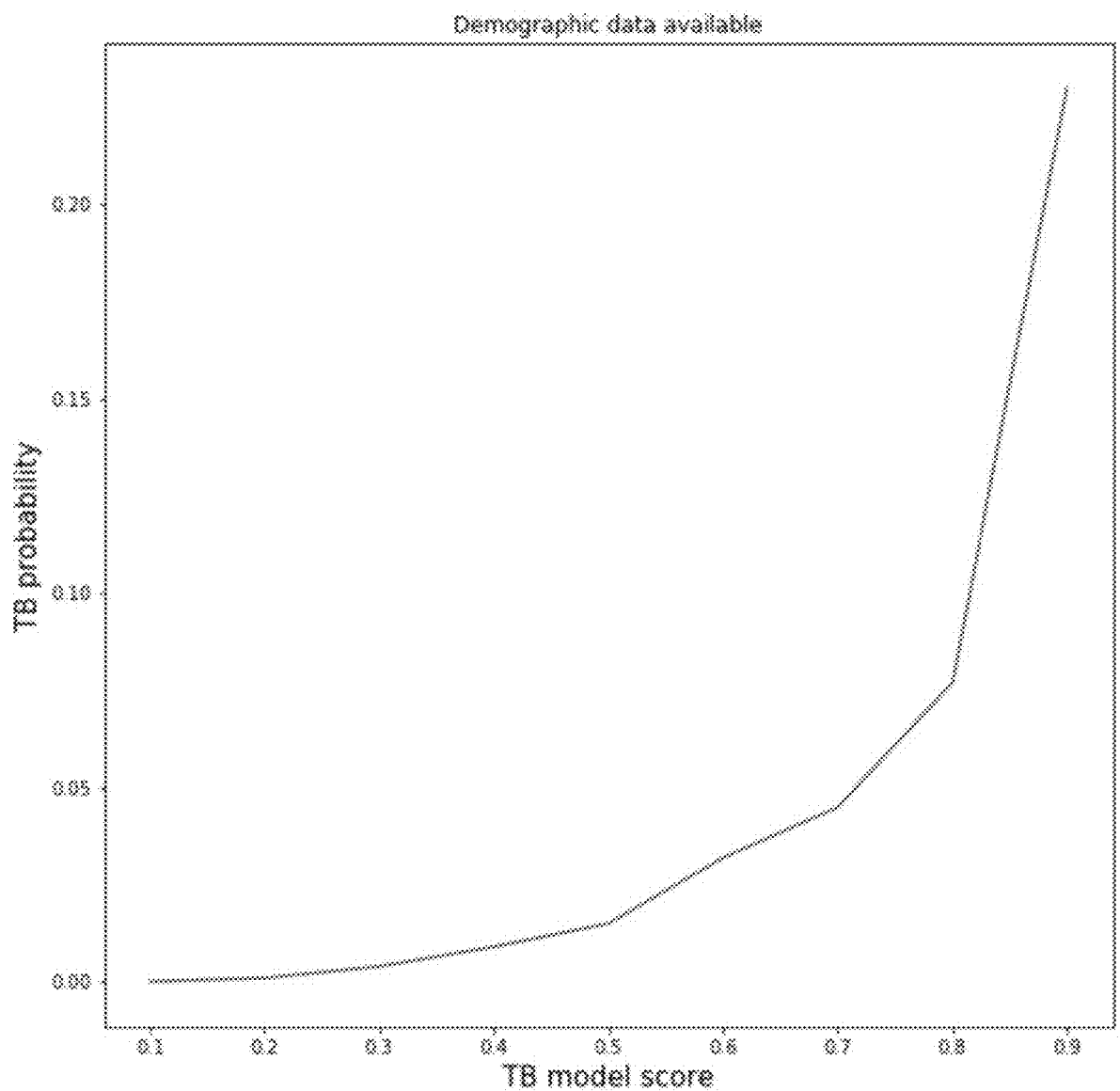
FIG. 6 An exemplary TB probability curve with known population statistics.
Figure 7:
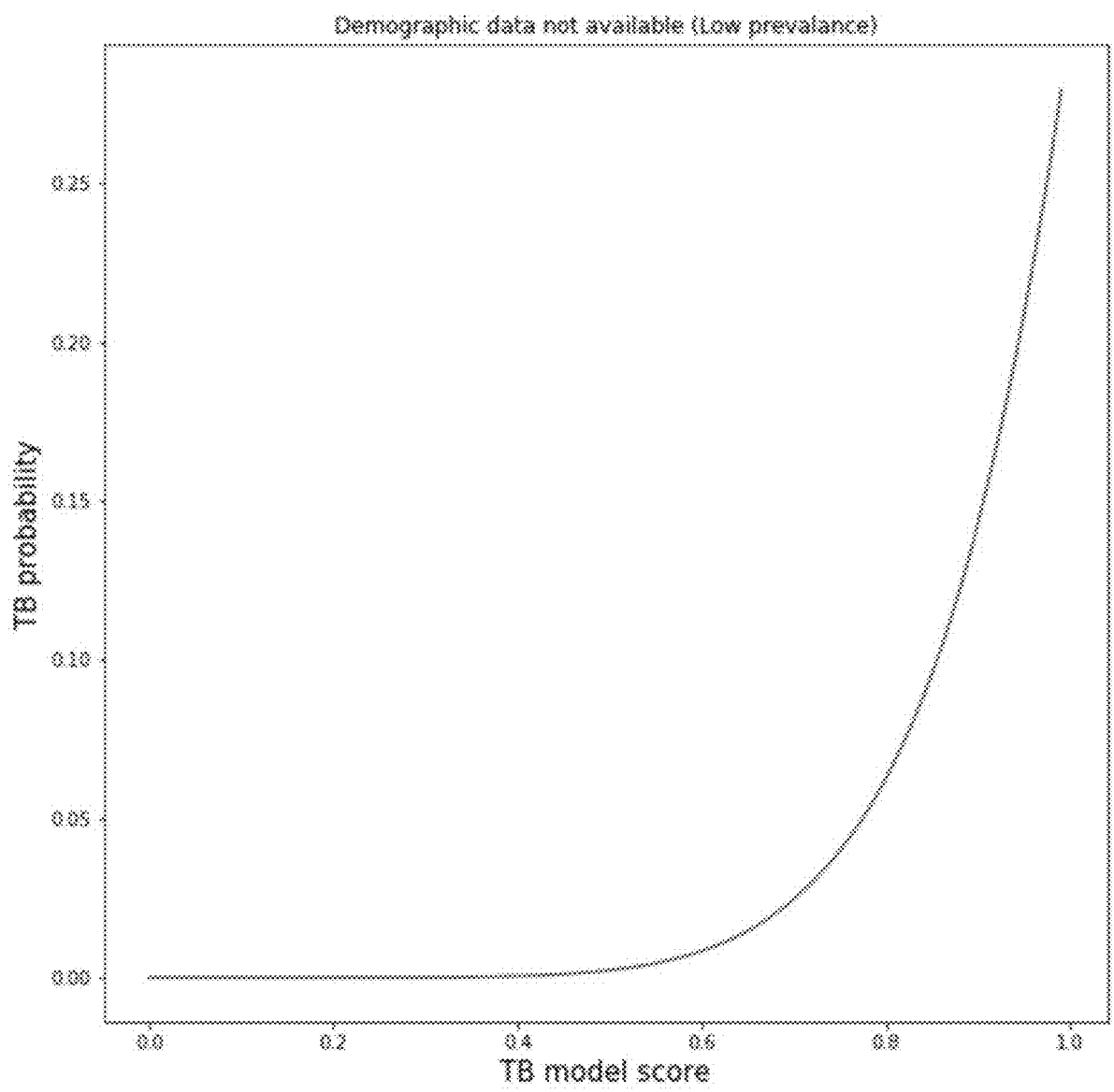
FIG. 7 An exemplary TB probability curve with low prevalence rate.
Figure 8:
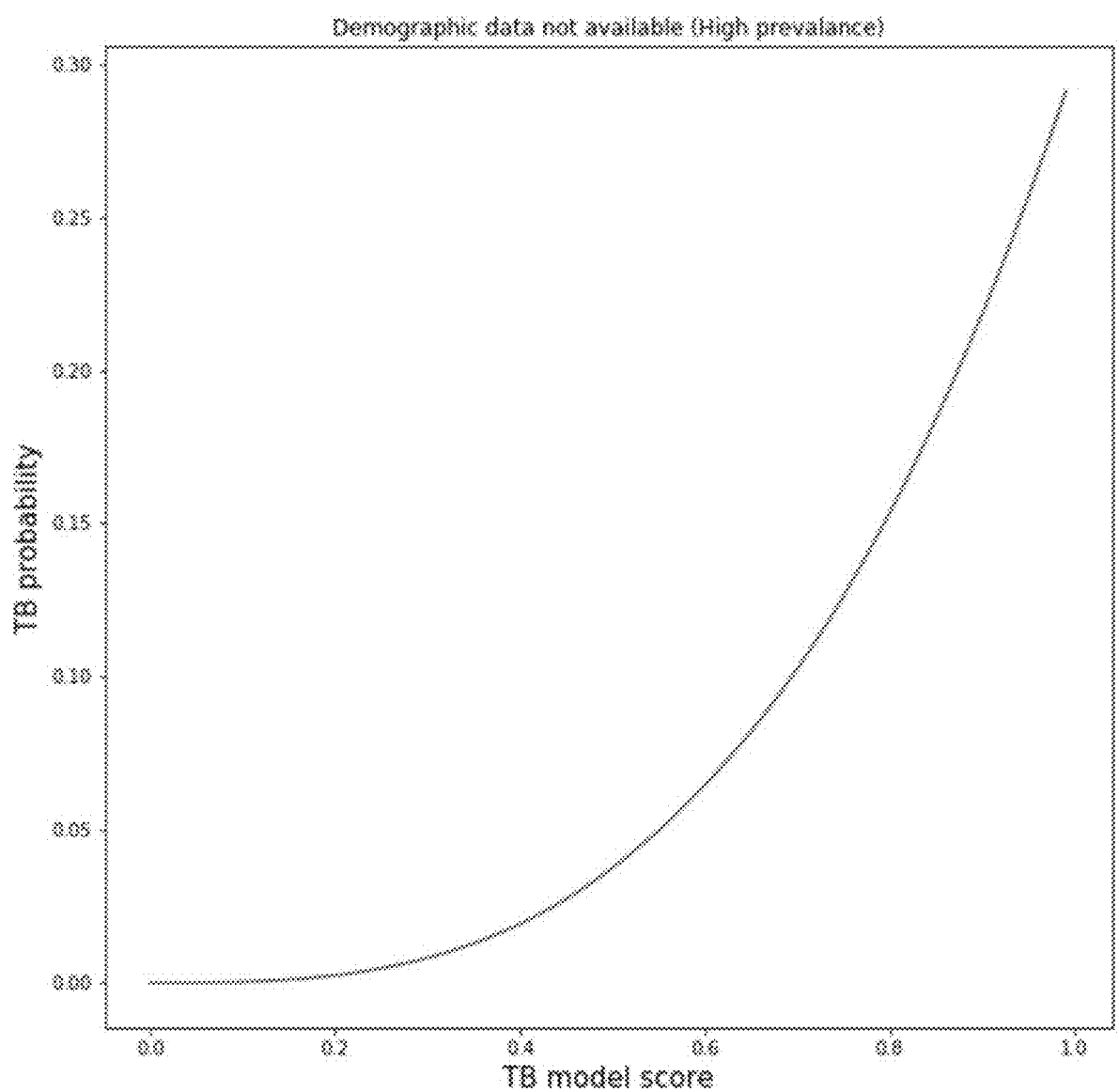
FIG. 8 An exemplary TB probability curve with high prevalence rate.

To determine the probability that a subject is positive for TB, the TB score of each subject is mapped to the probability of a subject having TB based on the demographic prevalence data and/or retrospective data. For a demographic where the proprietary deep learning system has been deployed and retrospective data have been collected, this mapping is calculated from the data directly. An exemplary TB probability curve is shown in FIG. 6. If the population statistics data is unavailable, the TB score of each subject is mapped to the probability of a subject having TB based on prevalence rate in a geographic area. In a geographic area where the prevalence rate is very low, the probability curve rises steeply at a higher TB score as shown in FIG. 7, while the prevalence rate is high, the probability curve rises steeply even at a medium TB score as shown in FIG. 8.

To further confirm the subject for TB using a pooled molecular test, such as the Xpert assay, on the subject's sputum sample, the sputum sample of each subject is ranked from lowest to highest based on the TB score. The number of samples per pool is determined based on the collective probability of subjects having TB in a pool, wherein the collective probability is a sum of the probability of each subject having TB in the pool and wherein the collective probability is lesser than or equal to 1.

A chest X-ray scan triage strategy could potentially improve the affordability of Xpert for TB diagnosis, particularly in low-income countries and with enhanced case-finding.

The invention claimed is:

1. A method for detection of an infectious respiratory disease by implementation of an automated X-rays-based triage approach alongside algorithmic clinical sample pooling for molecular diagnosis, comprising:

receiving a clinical sample and chest X-ray scan imaging procedure data from a subject;

processing images from the chest X-ray scan imaging procedure data;

detecting and localizing medical abnormalities of the images using a deep learning system, generating a first score that corresponds to a level of recognition of each of the medical abnormalities and outputting a bounding box representing the precise location and extent of the medical abnormalities;

generating a second score for each subject that corresponds to a level of recognition of an infectious respiratory disease based on the first scores of the medical abnormalities that suggest a typical or atypical symptom of the infectious respiratory disease;

mapping the second score to a probability of a subject having the infectious respiratory disease;

ranking the clinical sample from lowest to highest based on the second score; and selecting a pooling size of clinical samples for a molecular test based on a collective probability of all the subjects having the infectious respiratory disease in a pool, wherein the collective probability is a sum of the probability of each subject having the infectious respiratory disease in the pool and wherein the probability is lesser than or equal to 1.

2. The method of claim 1, wherein the deep learning system carried out by a computer for analyzing chest X-ray scans is developed by the steps of:

selecting medical imaging scans and extracting the medical abnormalities using natural language processing (NLP) algorithms to generate extracted findings, wherein the extracted findings are used as labels for training a deep learning algorithm, wherein the medical abnormalities comprise blunted costophrenic angle, calcification, cardiomegaly, cavity, cervical rib, consolidation, hyper inflation, fibrosis, prominence in hilar region, opacity, pleural effusion, and scoliosis;

segmenting, via an anatomy segmenter, the selected chest X-ray imaging scans to generate segmentation masks corresponding to chest cavity, lungs, diaphragm, mediastinum and ribs;

outputting, via a region of interest (ROI) generator, a plurality of ROIs that are relevant for detecting a particular abnormality, wherein the ROI generator uses the chest X-ray imaging scan at full resolution and the corresponding anatomy segmentation masks; and detecting the abnormalities, via abnormality detector, and outputting a low-resolution probability map per each ROI, a confidence score per each ROI, and a confidence score for an entire chest X-ray scan by combining the confidence scores per each ROI, wherein the abnormality detector is a hybrid classification plus segmentation network.

3. The method of claim 1, wherein the infectious respiratory disease comprise tuberculosis, pertussis, Swine influenza (H1N1), Avian influenza (H5N1), Enterovirus infectious diseases, Influenza A, Influenza B, Bronchitis, Coronavius COVID-19 (SARS-CoV-2), Severe Acute Respiratory Syndrome (SARS), and Middle East Respiratory Syndrome (MERS).

4. The method of claim 2, wherein the extracted findings comprise locations, severity, size, shape and texture.

5. The method of claim 2, wherein the labels comprises scan level labels, ROI level labels, and pixel level labels.

6. The method of claim 2, wherein the NLP algorithms are rule-based.

7. The method of claim 1, wherein the deep learning algorithm comprises convolutional neural networks (CNNs).

8. The method of claim 2, wherein the anatomy segmenter uses a U-Net based neural network.

9. The method of claim 2, wherein the ROI generator is rule-based.

10. The method of claim 2, wherein the confidence scores per each ROI are combined using a pooling operator that is a convex approximation of LogSumExp (LSE) function.

11. The method of claim 1, wherein the system uses a weighted sum of cross entropy loss at three levels comprising ROI level predictions, pixel level probability maps, and final pooled chest X-ray scan level prediction.

12. The method of claim 2, wherein the abnormality detector is based on ResNeXT-50 with Squeeze-excitation modules (SE-Res NeXT-50).

13. The method of claim 1, wherein the medical abnormalities comprise blunted CP angle, calcification, cardiomegaly, cavity, consolidation, fibrosis, hilar enlargement, opacity and pleural effusion.

14. The method of claim 1, wherein the molecular diagnosis comprises detecting the presence of a nucleic acid disease marker and a protein disease marker.

15. The method of claim 1, wherein the clinical sample is a sputum sample.

16. The method of claim 1, wherein the molecular diagnosis is a real-time PCR assay that facilitates semiquantitative detection of infectious agents comprising *Mycobacterium tuberculosis* (MTB) and rifampin (RIF) resistance.

17. A system for detection of an infectious respiratory disease by implementation of an automated X-rays-based triage approach alongside algorithmic clinical sample pooling for molecular diagnosis, comprises a first subsystem for automating detection and localization of medical abnormalities on chest X-ray imaging scans using a deep learning algorithm carried out by a computer, wherein the deep learning algorithm is developed by the steps of:

receiving and processing images from the chest X-ray scan imaging procedure data;

detecting and localizing medical abnormalities of the images using a deep learning system, wherein the deep learning system carried out by a computer is developed by the steps of:

generating a first score that corresponds to a level of recognition of each of the medical abnormalities and outputting a bounding box representing the precise location and extent of the medical abnormalities; and generating a second score for each subject that corresponds to a level of recognition of an infectious respiratory disease based on the first scores of the medical abnormalities that suggest typical or atypical the infectious respiratory disease; and a second subsystem for algorithmic pooling of clinical samples from each subject who also receives chest X-ray scans, wherein the algorithmic pooling is carried out by a computer following the steps of:

mapping the second score derived from the first subsystem to a probability of a subject having the infectious respiratory diseases;

ranking the clinical samples from lowest to highest based on the second score; and selecting a pooling size of the clinical samples for a molecular test based on a collective probability of all the subjects having the infectious respiratory disease in a pool, wherein the collective probability is a sum of the probability of each subject having the infectious respiratory disease in the pool and wherein the probability is lesser than or equal to 1.

18. The system of claim 17, wherein the deep learning system carried out by a computer for analyzing chest X-ray scans is developed by the steps of:

selecting medical imaging scans and extracting the medical abnormalities using natural language processing (NLP) algorithms to generate extracted findings, wherein the extracted findings are used as labels for training a deep learning algorithm, wherein the medical abnormalities comprise blunted costophrenic angle, calcification, cardiomegaly, cavity, cervical rib, consolidation, hyper inflation, fibrosis, prominence in hilar region, opacity, pleural effusion, and scoliosis;

segmenting, via an anatomy segmenter, the selected chest X-ray imaging scans to generate segmentation masks corresponding to chest cavity, lungs, diaphragm, mediastinum and ribs;

outputting, via a region of interest (ROI) generator, a plurality of ROIs that are relevant for detecting a particular abnormality, wherein the ROI generator uses the chest X-ray imaging scan at full resolution and the corresponding anatomy segmentation masks; and detecting the abnormalities, via abnormality detector, and outputting a low-resolution probability map per each ROI, a confidence score per each ROI, and a confidence score for an entire chest X-ray scan by combining the confidence scores per each ROI, wherein the abnormality detector is a hybrid classification plus segmentation network.

19. The system of claim 17, wherein the infectious respiratory diseases comprise tuberculosis, pertussis, Swine influenza (H1N1), Avian influenza (H5N1), Enterovirus infectious diseases, Influenza A, Influenza B, Bronchitis, Coronavius COVID-19 (SARS-CoV-2), Severe Acute Respiratory Syndrome (SARS), and Middle East Respiratory Syndrome (MERS).

20. The system of claim 18, wherein the extracted findings comprise locations, severity, size, shape and texture.

21. The system of claim 18, wherein the labels comprises scan level labels, ROI level labels, and pixel level labels.

22. The system of claim 18, wherein the NLP algorithms are rule-based.

23. The system of claim 17, wherein the deep learning algorithm comprises convolutional neural networks (CNNs).

24. The system of claim 18, wherein the anatomy segmenter uses a U-Net based neural network.

25. The system of claim 18, wherein the ROI generator is rule-based.

26. The system of claim 18, wherein the confidence scores per each ROI are combined using a pooling operator that is a convex approximation of LogSumExp (LSE) function.

27. The system of claim 17, wherein the system uses a weighted sum of cross entropy loss at three levels comprising ROI level predictions, pixel level probability maps, and final pooled chest X-ray scan level prediction.

28. The system of claim 18, wherein the abnormality detector is based on ResNeXT-50 with Squeeze-excitation modules (SE-ResNeXT-50).

29. The system of claim 17, wherein the medical abnormalities comprise blunted CP angle, calcification, cardiomegaly, cavity, consolidation, fibrosis, hilar enlargement, opacity and pleural effusion.

30. The system of claim 17, wherein the clinical sample is a sputum sample.

31. The system of claim 17, wherein the molecular diagnosis comprises detecting the presence of a nucleic acid disease marker and a protein disease marker.

32. The system of claim 17, wherein the molecular diagnosis is a real-time PCR assay that facilitates semiquantitative detection of infectious agents comprising *Mycobacterium tuberculosis* (MTB) and rifampin (RIF) resistance.

\* \* \* \* \*